United States Patent
Furnas

(10) Patent No.: US 7,781,723 B1
(45) Date of Patent: *Aug. 24, 2010

(54) CONTAINER INSPECTION MACHINE USING LIGHT SOURCE HAVING SPATIALLY CYCLICALLY CONTINUOUSLY VARYING INTENSITY

(75) Inventor: William J. Furnas, Elmira, NY (US)

(73) Assignee: Emhart Glass S.A., Cham (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/318,249

(22) Filed: May 25, 1999

Related U.S. Application Data

(63) Continuation-in-part of application No. 09/026,311, filed on Feb. 19, 1998, now Pat. No. 6,031,221.

(51) Int. Cl.
B07C 5/12 (2006.01)
G01N 21/00 (2006.01)

(52) U.S. Cl. .............................. 250/223 B; 356/239.4; 209/526

(58) Field of Classification Search ............. 250/223 B, 250/223 R, 559.4–559.46; 356/239.1, 239.4, 356/239.5, 239.7, 239.8, 240.1; 209/524, 209/526

See application file for complete search history.

(56) References Cited

U.S. PATENT DOCUMENTS

| | | | |
|---|---|---|---|
| 4,175,236 A * | 11/1979 | Juvinall | 250/566 |
| 4,601,395 A * | 7/1986 | Juvinall et al. | 209/526 |
| 4,601,398 A | 7/1986 | Solomon | |
| 4,924,083 A * | 5/1990 | Ishikawa et al. | 250/223 B |
| 5,004,909 A * | 4/1991 | Fukuchi | 250/223 B |
| 5,243,400 A | 9/1993 | Ringlien | |
| 5,822,053 A | 10/1998 | Thraikill | |

FOREIGN PATENT DOCUMENTS

| | | |
|---|---|---|
| DE | 68923653 | 5/1989 |
| EP | 0016551 | 2/1980 |
| EP | 0337421 | 10/1989 |
| EP | 0491555 | 12/1991 |
| EP | 0644417 | 9/1994 |
| EP | 0711995 A2 | 5/1996 |
| GB | 2157824 | 10/1985 |
| JP | 4220551 | 11/1992 |
| JP | 05209734 | 8/1993 |
| JP | 05223746 | 8/1993 |
| JP | 07110302 | 10/1993 |
| JP | 11108844 | 12/1993 |
| JP | 08178855 | 12/1996 |
| WO | 9106846 | 5/1991 |

* cited by examiner

Primary Examiner—Thanh X Luu
(74) Attorney, Agent, or Firm—Reinhart Boerner Van Deuren s.c.

(57) ABSTRACT

A machine is disclosed for inspecting the wall of a bottle which is delivered by a conveyor sequentially to an inspection station. A light source defines a plurality of vertical row groups each having no black row, a white row and a plurality of adjacent rows where the intensity systematically decreases to a lowest level where light blocking defects can be seen and than increases systematically to the next white row.

5 Claims, 2 Drawing Sheets

CONTAINER INSPECTION MACHINE USING LIGHT SOURCE HAVING SPATIALLY CYCLICALLY CONTINUOUSLY VARYING INTENSITY

This application is a continuation-in-part of my patent application Ser. No. 09/026,311 filed Feb. 19, 1998, now U.S. Pat. No. 6,031,221.

The present invention relates to a machine for inspecting glass or plastic containers such as bottles and more particularly to such a machine which can inspect the sidewall of the container to find defects.

BACKGROUND OF THE INVENTION

The side wall of a glass container can include various types of defects, including an area of unevenness in glass distribution which will provide a lensing effect when backlit (a refractive defect). Container inspection machines, such as shown in U.S. Pat. No. 5,004,909, inspect the sidewall of a glass bottle by presenting the bottle in front of a light source defined by alternating black and white stripes. Such an inspection machine can find refractive best when they are located at the edge of the stripe. Container inspection machines, such as shown in U.S. Pat. No. 4,601,395, inspect the sidewall of a glass container by presenting the bottle in front of a light source defined by a single bright area that is always in the view of the camera, with transversely spaced outer regions of various intensities and rotating the container.

OBJECT OF THE INVENTION

It is an object of the present invention to provide a container inspecting machine which will identify a light blocking defect when inspecting also for refractive defects.

Other objects and advantages of the present invention will become apparent from the following portion of this specification and from the accompanying drawings which illustrate in accordance with the mandate of the patent statutes a presently preferred embodiment incorporating the principles of the invention.

BRIEF DESCRIPTION OF THE PREFERRED EMBODIMENT

Figure 1:
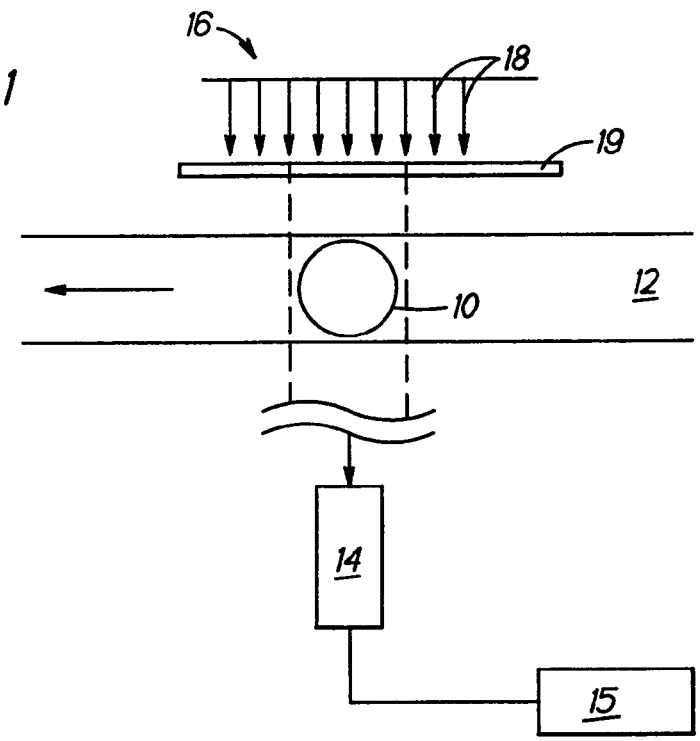
FIG. 1 is a top view of a container inspection machine made in accordance with the teachings of the present invention.

A bottle 10, which can be either glass or plastic is conveyed from right to left along a conveyor 12 for inspection at the illustrated inspection station where the bottle is imaged on the image of a CCD camera 14. The image is evaluated to identify anomalous pixel readings which are indicative of a defect. Associated with the CCD camera is a controlled light source 16 which defines a large area of light with a large number of vertical rows of L.E.D.s 18 (in the preferred embodiment). As can be seen from FIG. 1, the L.E.D.s are focused or aimed so that light will pass through the entire bottle (from top to bottom and from side to side) and be imaged on the camera. These vertical rows also are supported to emit light parallel to each other. Each vertical row of L.E.D.s 18 is turned on and off with a field effect transistor (not shown).

Figure 3:
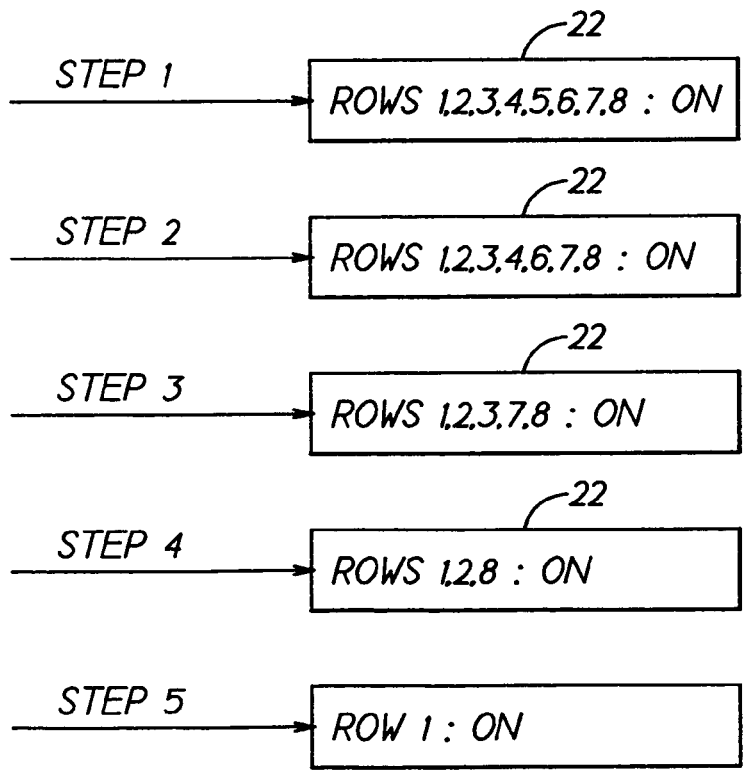
FIG. 3 is a schematic illustration showing the operation of the light source as implemented.
Figure 2:
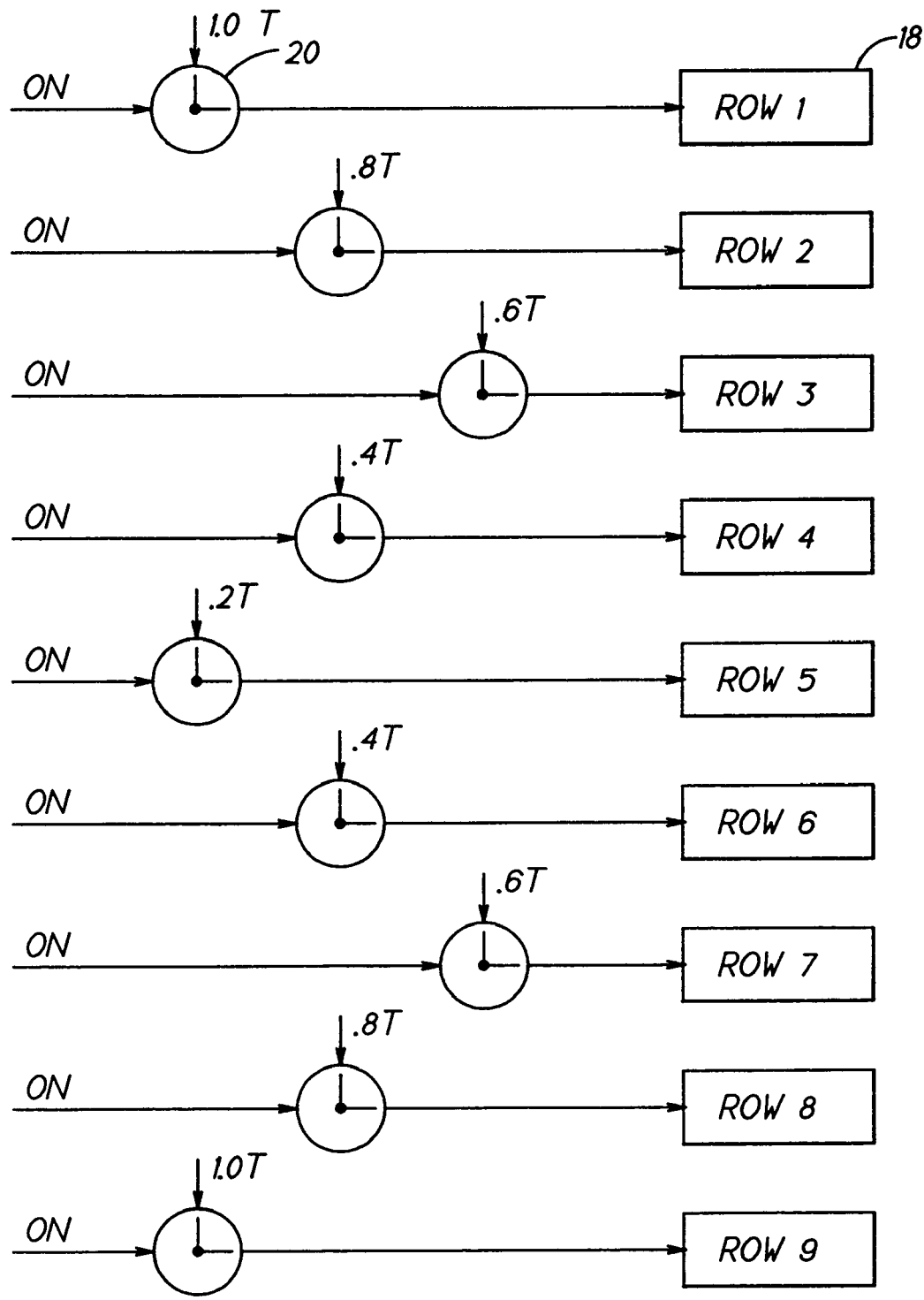
FIG. 2 is schematic representation showing the operation of the light source shown in FIG. 1.

In FIG. 2, individual timers 20 are connected to each vertical row of L.E.D.'s 18 so that when the rows are turned on, the timers will time out at selected times (0T,0.2T,0.4T,0.6T, and 0.8T) of an imaging cycle (the time T required for the row of L.E.D.'s to turn fully on and appear white) with light intensity being a function of the time on. In FIG. 3, a single control operates eight rows and defines bit masks 22 which turn on the desired vertical rows for each of four repeated equally timed steps (each step continues for 0.2T) of an imaging cycle to achieve the same result. The image is defined over the period of these four steps. While these illustrations discuss the use of time to set the desired intensity level, current level could alternately be controlled for the same purpose.

As can be seen from FIG. 2, the light source is made up of a number of vertical row groups, each having eight vertical rows. These eight rows proceed from bright to 0.8 bright, to 0.6 bright, to 0.4 bright, to 0.2 bright and then to 0.4 bright to 0.6 bright to 0.8 bright. While there are five intensity levels (20%, 40%, 60%, 80% and 100%) in the illustrated embodiments, other numbers can be used. By setting the minimum intensity level (20%) high enough so that light blocking defects can be identified, both light blocking defect and refractive defects can be simultaneously identified by the CCD camera over 100% of the area of the light source.

A bottle 10, which can be either glass or plastic is conveyed from right to left along a conveyor 12 for inspection at the illustrated inspection station where the bottle is imaged on the image of a CCD camera 14. The image is evaluated to identify anomalous pixel readings which are indicative of a defect. Associated with the CCD camera is a controlled light source 16 which defines a large area of light. In the preferred embodiment there are a large number of vertical rows of L.E.D.s 18. As can be seen from FIG. 1, the L.E.D.s are focused or aimed so that light will pass through the entire bottle (from top to bottom and from side to side) and be imaged on the camera. These vertical rows also are supported to emit light parallel to each other and the emitted light passes through a diffuser element. Each vertical row of L.E.D.s 18 is turned on and off with a field effect transistor or the like (not shown).

In FIG. 2, an individual timer 20 is connected to each field effect transistor so that when each row can be turned on for a selected time. The timers will time out at selected times (0.2T,0.4T,0.6T,0.8T,1.0T) of an imaging cycle (here time is equated to the ideal time required for the row of L.E.D.'s to appear illuminated to a selected degree) with light intensity being a function of the time on. For example, 0.60T is the time that a vertical row of lights must be on for the intensity of the row to appear 60%. For discussion purposes the light of a fully on source is referred to as "white", but it should be understood that the light source may be colored and the illuminated light may in fact be invisible (an infrared L.E.D. for example). Actual "on" times may also be varied to compensate for overlapping illumination effects. Due to overlap of light output, actual "on" times, for a particular column, may need to be modified to achieve a best fit to the desired continuously varying intensity cycle. For example, the full bright (1.0T) columns, which may not get full white because they are getting only partial light from neighboring 0.8T columns may need to be set at an increased time on (1.15T, for example). Calculations based upon the actual performance of the illumination method, in this case, L.E.D./diffuser combination, will determine the method of calculating corrections to produce the desired spatially cyclically continuously varying intensity between the extremes of dark and light intensity source.

As shown in FIG. 3, a single control operates eight rows and defines bit masks 22 which turn on the desired vertical rows for each of each of the four repeated timed steps (as illustrated each step continues for 0.2T) of an imaging cycle. The image is defined over the period of these five steps. While these illustrations discuss the use of time to set the desired intensity level, current level could alternately be controlled for the same purpose. Other light sources can be used with various light output control over the area methods, such as LCD panel, or printed pattern, in conjunction with a shuttered camera for the same purpose. While there are five intensity levels (20%, 40%, 60%, 80% and 100%) in the illustrated embodiments, other numbers can be used. A spatially cyclically continuously varying intensity between the 20% bright and light is defined on the light source illumination area which cyclically changes at a rate of change which is less than that required to be detected as a defect. The minimum brightness level (20%) is choosen so that either a light blocking defect or a refractive defect can be identified by the CCD camera over 100% of the area of the light source.

As can be seen from FIG. 3, full control over the individual column intensity goes beyond the fractional linearly calculated percentage previously presented. The pattern presented here could be described as a triangle wave whose peak is a full bright and valley is at 20% bright. As can be seen from FIG. 3, full control over the number of columns going from 20% bright to bright can be controlled. Changing the number of columns can be done to optimize the cyclic nature of the pattern for a container size or defect size. The spatially varying intensity cycles may be horizontal or vertical or at some other angle. It may also be a combination of angles.

Full control over the relative position of the pattern to the overall backlight (and thus the container to be inspected) can also be controlled. Where the inspection process may use dynamically located zones, the bright portion of the pattern can be optimally placed to aid in the location of the container.

For a one axis cyclic variation, a measure of the light source quality would provide of a nearly flat histogram analysis of the source. A two axis light cyclic light source could also be used to generate such variations with individual LED control, using a transmissive light control scheme such as a light valve, LCD, or printed pattern. A computer 15 analyzes the camera image by comparing neighboring pixels (one or more away) alone or in combination to determine the rate of change in intensity to identify defects where the rate of change exceeds a defined value.

The invention claimed is:

1. A machine for inspecting the wall of a bottle comprising a conveyor for supporting a bottle at an inspection station, the inspection station including
a CCD camera on one side of the conveyor having a camera image,
a light source, on the other side of the conveyor, for imaging the bottle on said CCD camera image,
wherein said light source comprises a plurality of L.E.D. rows, and
wherein said plurality of L.E.D. rows define a plurality of row groups each including a row having a maximum brightness level, a row having a minimum brightness level, at least one row intermediate said row having said maximum brightness level and said row having said minimum brightness level having a brightness level between said minimum brightness level and said maximum brightness level, and at least one row on the side of the row having the minimum brightness level remote from said row having the maximum brightness level having a brightness level between the minimum brightness level and the maximum brightness level,
energy controlling means for operating said light source to emit light energy for defining light intensities varying between a minimum brightness level that will permit the identification of a light blocking defect and a maximum brightness level, the brightness level varying spatially, cyclically, and continuously at a rate of change which is less than a rate of change that would be identified as a defect,
computer means for analyzing the camera image by comparing neighboring pixels to determine the rate of change in brightness level to indentify defects where the rate of change exceeds a defined value.

2. A machine for inspecting the profile and wall of a bottle according to claim 1, wherein there are a plurality of vertical L.E.D. rows intermediate the row having the minimum brightness level and the row having the maximum brightness level and the brightness level of said plurality of intermediate rows uniformly reduces from the row having the maximum brightness level to the row having the minimum brightness level.

3. A machine for inspecting the profile and wall of a bottle according to claim 2, wherein there are a plurality of vertical L.E.D. rows on the side of said row having the minimum brightness level remote from said row having the maximum brightness level and the brightness level of said plurality of said rows on the side of said row having the minimum brightness level remote from said row having the maximum brightness level uniformly increasing in brightness level proceeding away from the row having the minimum brightness level.

4. A machine for inspecting the profile and wall of a bottle according to claim 3, wherein the row having the minimum brightness level has a brightness level of about 20% of the maximum brightness level and where each of said vertical L.E.D. row groups has three vertical rows intermediate the row having the minimum brightness level and the row having the maximum brightness level, with the row adjacent the row having the minimum brightness level having a brightness level of about 40% of the maximum brightness level and the row adjacent the row having the maximum brightness level having a brightness level of about 80% of the maximum brightness level and the intermediate of the three vertical rows intermediate the row having the minimum brightness level and the row having the maximum brightness level having a brightness level of about 60% of the maximum brightness level.

5. A machine for inspecting the profile and wall of a bottle according to claim 4, wherein each of said vertical L.E.D. row groups has three vertical rows on the side of the row having the minimum brightness level remote from the row having the maximum brightness level, with the row adjacent the row having the minimum brightness level remote from the row having the maximum brightness level having a brightness level of about 40% of the maximum brightness level and the next of the three vertical rows on the side of the row having the minimum brightness level remote from the row having the maximum brightness level having a brightness level of about 60% of the maximum brightness level and the last of the three vertical rows on the side of the row having the minimum brightness level remote from the row having the maximum brightness level having a brightness level of about 80% of the maximum brightness level.

* * * * *